United States Patent [19]

Fowler

[11] Patent Number: 4,992,446
[45] Date of Patent: Feb. 12, 1991

[54] TRICYCLIC QUINOLIZINE AMIDES
[75] Inventor: Kerry W. Fowler, Seattle, Wash.
[73] Assignee: G. D. Searle & Co., Chicago, Ill.
[21] Appl. No.: 402,955
[22] Filed: Sep. 5, 1989
[51] Int. Cl.$^5$ .................. A61K 31/435; C07D 455/02
[52] U.S. Cl. ....................................... 514/294; 546/95
[58] Field of Search ........................... 546/95; 514/294
[56] References Cited

U.S. PATENT DOCUMENTS

| | | | |
|---|---|---|---|
| 3,907,810 | 9/1975 | Cavalla et al. | 546/210 |
| 3,910,931 | 10/1975 | Cavalla et al. | 514/326 |
| 3,910,932 | 10/1975 | Cavalla et al. | 514/326 |
| 3,912,741 | 10/1975 | Cavalla et al. | 514/326 |
| 3,917,614 | 11/1975 | Cavalla et al. | 514/326 |
| 3,919,242 | 11/1975 | Cavalla et al. | 514/326 |
| 4,028,365 | 6/1977 | Cavalla et al. | 514/326 |
| 4,029,801 | 6/1977 | Cavalla et al. | 514/326 |
| 4,045,444 | 8/1977 | Cavalla et al. | 514/326 |
| 4,046,767 | 9/1977 | Cavalla et al. | 514/326 |
| 4,061,640 | 12/1977 | Cavalla et al. | 514/326 |
| 4,102,886 | 7/1978 | Szántay et al. | 546/95 |
| 4,138,492 | 2/1979 | Noverola et al. | 544/335 |
| 4,183,937 | 1/1980 | Ward | 546/95 |
| 4,193,998 | 3/1980 | Szántay et al. | 546/95 |
| 4,277,501 | 7/1981 | Molley et al. | 564/374 |
| 4,289,781 | 9/1981 | Bengtsson et al. | 546/200 |
| 4,304,913 | 12/1981 | Havera et al. | 546/95 |
| 4,596,827 | 6/1986 | Molley et al. | 514/605 |
| 4,604,398 | 8/1986 | Ward | 546/95 |
| 4,686,226 | 8/1987 | Huff et al. | 546/95 |

FOREIGN PATENT DOCUMENTS 1345872 2/1974 United Kingdom .
2106909 4/1983 United Kingdom .
2160862 1/1986 United Kingdom .

OTHER PUBLICATIONS

Fleming et al., Hypertension-Anthypertensive Drugs, Abstract 1567.
Hanson et al., Hypertension-Antihypertensive Drugs, Abstract 1570.
Bobbitt et al., The Journal of Organic Chem., vol. 33, pp. 2958-2959 (1968).

Primary Examiner—Cecilia Shen
Attorney, Agent, or Firm—Joy Ann Serauskas; Paul D. Matukaitis

[57] ABSTRACT

Tricyclic quinolizine amides, which have activity as Class III antiarrhythmic agents, acting by prolonging cardiac action potential repolarization. The invention further provides for compositions incorporating the compounds and methods of their use, as well as providing for pharmaceutically acceptable salts of the compounds.

31 Claims, No Drawings

TRICYCLIC QUINOLIZINE AMIDES

BACKGROUND OF THE INVENTION

The present invention provides novel compounds, novel compositions, methods of their use and methods of their manufacture, such compounds pharmacologically useful in the treatment of cardiac arrhythmias. More specifically, the compounds of the present invention are Class III antiarrhythmic agents which, by effectively prolonging repolarization of a cardiac cell action potential, can be used effectively to treat certain cardiac arrhythmias.

Antiarrhythmic drugs have been grouped together according to the pattern of electrophysiological effects that they produce and/or their presumed mechanisms of action. Thus, Class I antiarrhythmic agents are characterized by being sodium channel blockers, Class II antiarrhythmic agents are beta-adrenergic blockers, Class III antiarrhythmic agents prolong repolarization, and Class IV antiarrhythmic agents are calcium channel blockers.

Currently, there are very few Class III antiarrhythmic agents available for theraputic use. Among them is bretylium. Bretylium's usefulness is limited, however, and currently its theraputic use is reserved for life-threatening ventricular arrhythmias that are refractory to other therapy. Thus, bretylium's use is generally confined to intensive care units. It is an object of this invention to provide Class III antiarrhythmic agents of broader theraputic use than existing Class III antiarrhythmic agents.

SUMMARY OF THE INVENTION

The invention relates to novel compounds of the general formula I:

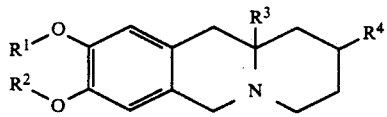

the pharmaceutically acceptable salts thereof, and the hydrated forms thereof, wherein $R^1$ and $R^2$ are independently alkyl, alkenyl or alkynyl of from 1 to 10 carbon atoms; $R^3$ is hydrogen in either a cis or a trans orientation; and $R^4$ is NHCOR' in either a cis or a trans orientation, wherein R' is alkyl, alkenyl or alkynyl of from 1 to 10 carbon atoms, cycloalkyl of from 3 to 8 carbon atoms, phenyl, phenyl substituted by alkyl, alkenyl or alkynyl of one to ten carbon atoms or alkoxy having alkyl, alkenyl or alkynyl of from one to ten carbon atoms, halogen, or amino, fused phenylcycloalkyl, fused phenylcycloalkyl wherein phenyl is substituted by alkyl, alkenyl or alkynyl of from one to ten carbon atoms, benzofuranyl or benzofuranyl substituted by alkyl, alkenyl or alkynyl of from one to ten carbon atoms.

The compounds and pharmaceutical compositions thereof are useful in the antiarrhythmic methods of the invention. The invention further provides dosage unit forms adapted for oral, topical and parenteral administration. Also provided for in this invention are the pharmaceutically acceptable salts of the compounds.

DETAILED DESCRIPTION OF THE INVENTION

As used herein, the term "alkyl" is defined to include straight or branched chain carbon-carbon linkages of one to ten carbon atoms. "Alkenyl" shall have the same meaning, except that one or more double bonds can be present therein. "Alkynyl" shall have the same meaninq, except that one or more triple bonds can be present therein. The term "cycloalkyl" is defined to include cyclic carbon-carbon rings of three to eight carbon atoms.

The term "alkoxy" is defined to include alkyl, alkenyl and alkynyl of from one to ten carbon atoms.

The term "halogen" shall include fluorine, chlorine, bromine and iodine.

The term "benzofuranyl" is defined to mean the substituent of the formula

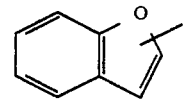

The term "cardiac arrhythmia" is defined to mean any variation from the normal rhythm of the heartbeat, including, without limitation, sinus arrhythmia, premature heartbeat, heartblock, fibrillation, flutter, pulsus alternans, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

The term "pharmaceutically acceptable salts" refers to non-toxic salts of the compounds of this invention which are generally prepared by reacting the free base with a suitable organic or inorganic acid. Representative salts include the hydrochloride, hydroiodic, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

Compounds of the invention can be prepared readily according to the following reaction scheme or modifications thereof using readily available starting materials, reagents and conventional synthesis procedures. In these reactions, it is also possible to make use of variants which are in themselves known, but are not mentioned in greater detail.

Scheme 1

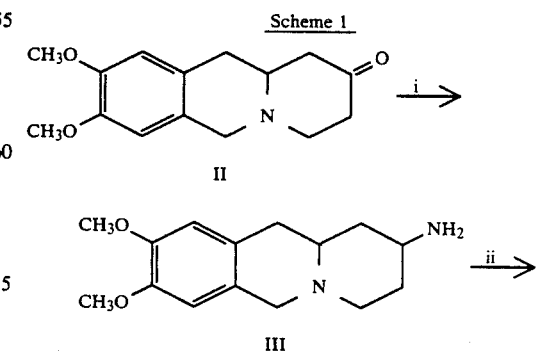

-continued
Scheme 1

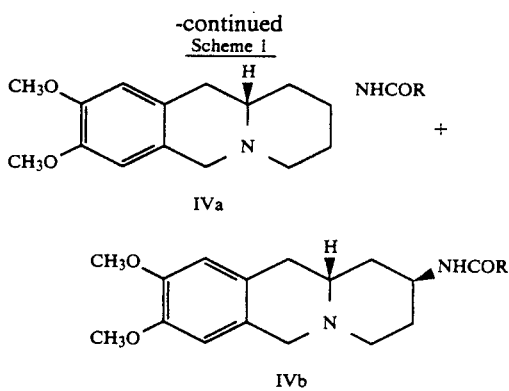

i. NH$_4$OAc, Pd/C, H$_2$, EtOH, rt.
ii. RCOCl, pyridine, 0° C.,

The compounds of the present invention can be administered in such oral dosage forms as tablets, capsules, pills, powders, granules, elixers, tinctures, suspensions, syrups and emulsions. Likewise, they can also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the treatment of arrhythmias of the heart. The dosage regimen utilizing the compounds of the present invention is selected in accordance with a variety of factors including the type, species, age, weight, sex and medical condition of the patient; with the severity of the condition to be treated; the route of administration; the renal and hepatic function of the patient; and the particular compound employed or salt thereof. An ordinarily skilled veterinarian or physician can readily determine and prescribe the effective amount of the drug required to prevent, treat or arrest the progress of the condition.

Oral dosages of the compounds of the present invention, when used for the indicated cardiac effects, will range between about 0.lmg per kilogram of body weight per day (mg/kg/day) to about 1000 mg/kg/day and preferably 1.0 to 100 mg/kg/day. Advantageously, the compounds of the present invention can be administered in a single daily dose or the total daily dosage can be administered in divided doses of two, three or four times daily.

In the pharmaceutical compositions and methods of the present invention, the compounds described in detail below form the active ingredient that can typically be administered in admixture with suitable pharmaceutical diluents, excipients or carriers (collectively referred to herein as "carier" materials) suitably selected with respect to the intended form of administration, that is, oral tablets, capsules, elixers, syrups and the like, and consistent with conventional pharmaceutical practices.

For instance, for oral administration in the form of tablets or capsules, the active drug component can be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug component can be combined with any oral non-toxic pharmaceutically acceptable inert carrier such as ethanol, glycerol, water, and the like. In the case of oral administration and in liquid form, suitable flavoring carriers can be added such as cherry syrup and the like. Moreover, when desired or necessary, suitable binders, lubricants, disintegrating agents and coloring agents can also be incorPorated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol and various waxes. Lubricants for use in these dosage forms include magnesium stearate, sodium benzoate, sodium acetate, sodium stearate, sodium chloride, sodium oleate and the like. Disintegrators include, without limitation, starch, methylcellulose, agar, bentonite, xanthan gum and the like.

The compounds of this invention can also be administered by intravenous route in doses ranging from 0.01 to 10 mg/kg/day.

Furthermore, it is also contemplated that the invention can be administered in an intranasal form topically via the use of suitable intranasal vehicles, or via transdermal routes, using those forms of transdermal skin patches well known to those of ordinary skill in that art. In the case of transdermal skin patch administration, daily dosage is continuous via the transdermal delivery system rather than divided, as in an oral delivery system.

The compounds of this invention exhibit antiarrhythmic activity useful in the treatment of various cardiac arrhythmias. The test procedures employed to measure this activity of the compounds of the present invention are described below.

EXAMPLE 1

Guinea pigs, of either sex weighing between 200–350 g, are acutely sacrificed and the right ventricular papillary muscle is isolated. A sample of a given test compound is added using an in vitro tissue bath. Concentrations used are generally $3 \times 10^{-5}$M, but may also be as low as $3 \times 10^{-7}$M. Changes in refractory period are measured before and after adding 1 concentration (usually $3 \times 10^{-5}$M, as noted above) of a test compound to the bath. One hour is allowed for drug equilibration. A compound is considered active (Class III) if an increase in ventricular refractory period is 25msec or more (at $3 \times 10^{-5}$M).

| Compound | Results Concentration (M) | Change (msec) |
| --- | --- | --- |
| H$_2$O | 0 | 8 |
| Disopyramide | $3 \times 10^{-5}$ | 20 |
| Clofinium | $3 \times 10^{-5}$ | 24 |
| Sotalol | $3 \times 10^{-5}$ | 35 |
| Example 3, component A | $3 \times 10^{-5}$ | 80 |
| Example 3, component B | $3 \times 10^{-5}$ | 55 |
| Example 4, component A | $3 \times 10^{-5}$ | 45 |
| Example 5, component A | $3 \times 10^{-5}$ | 55 |
| Example 5, component B | $3 \times 10^{-7}$ | 50 |

The following non-limiting examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Melting points were determined on a Thomas-Hoover Unimelt Capillary Apparatus and are not corrected. Unless otherwise noted, I.R. and NMR spectra were consistent with the assigned structure.

The compounds of this invention may be prepared by the method illustrated in Scheme 1. Unless otherwise specified, the various substituents are defined as for formula I above.

Tricyclic ketones of formula II are prepared by methods well known to those of ordinary skill in the art. (J. M. Bobbitt and T. E. Moore, *J. Org. Chem.* 1968, 33, 2958; S. F. Dyke, C. R. Spray, and R. A. Kilminster, *Aust. J. Chem.* 1983, 36, 149). Reductive amination of the intermediates of formula II affords primary amines of formula III. A preferred method employs ammonium acetate in the presence of 10% palladium on carbon catalyst at 60 psi of hydrogen gas pressure at room temperature. Alternative preferred acylating conditions employ a carboxylic acid chloride, a carboxylic acid activated as the mixed anhydride, or the carboxylic ester activated by alkylaluminum reagents.

The amide intermediates of formula IVa or IVb can be subsequently converted to the quaternary salts by suitable N-alkylating reagents (where a suitable leaving group is present, such as halogen, mesylate, or tosylate). Preferred alkylation conditions employ acetonitrile as the solvent at room temperature.

EXAMPLE 2

Synthesis of 1,3,4,6,11,11a-hexahydro-9-dimethoxy-2H-benzo[b]-quinolizin-2-amine The ketone 8,9-dimethoxy-1,3,4,6,11,11a-hexahydro-2H-benzo [b]quinolizin-2-one was prepared as previously described (J. M. Bobbitt and T. E. Moore, *J. Org. Chem.* 1968, 33, 2958; S. F. Dyke, C. R. Spray, and R. A. Kilminster, *Aust. J. Chem.* 1983, 36, the entire disclosure of which is incorporated herein by reference, 149). A solution of 2.5 g of this ketone in 100 mL EtOH was hydrogenated at a pressure of 60 psi at room temperature over 0.375 g of 10% palladium on carbon catalyst. After 5.5 h the uptake of hydrogen was complete and solvent was removed in vacuo from the filtered reaction mixture. Partitioning of the residue between chloroform and dilute aqueous NaOH and removal of the solvent afforded 2 71 g of a crude foam which was purified by flash chromatography. The product, 1.57 g of tan solid (63%), was a mixture of diastereomers used directly in subsequent acylations.

Anal. calcd. for $C_{15}H_{22}N_2O_2$:
C,68.67;H,8.45;N,10.68. Found C,67 90;H,8.37;N,10.40.

$^1$H NMR (CDCl$_3$) 6 6.56 (s,1), 6.52 (s,1), 3.84 (s, 6, OMe)

EXAMPLE 3 trans-N-(8,9-dimethoxy-1,3,4,6,11,11a-hexahydro-2H-benzo[b] quinolizin-2-yl)benzamide

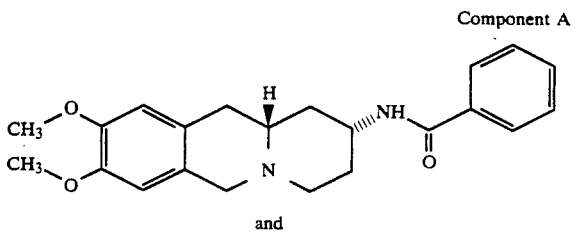

Component A cis-N-(8,9-dimethoxy 1,3,4,6,11,11a-hexahydro-2H-benzo[b] quinolizin-2-yl)benzamide

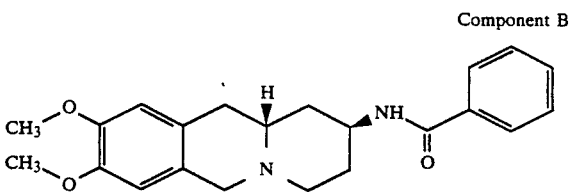

Component B

A Solution of 8,g-dimethoxy-1,3,4,6,11,11a-hexahydro-2H-benzo [b]-quinolizin-2-amine (1.16 g) in pyridine (15 mL) was cooled in an ice bath and treated with benzoyl chloride (0.65 mL). The reaction mixture was allowed to stir for 2.5 h and was poured into dil. aqueous NaOH, extracted three times with 15 mL of chloroform, washed twice with 15 mL water and once with saturated brine 15 mL to afford, after removal of solvent, 1.92 g of tan solid. Flash chromatography (70:28:2 cyclohexane:isopropanol: NH$_4$OH) provided two diastereomeric compounds, a higher R$_f$ product (A, 0.54 g), and a lower R$_f$ Product (B, 0.49 g). Recrystallization of each component from ethyl acetate/hexane afforded pure products.

Component A, mp 215–218° C. (corr) was identified by $^1$H NMR as the trans compound IVa (R=Ph). Anal. calc'd. for $C_{22}H_{26}N_2O_3$: C,72.11;H,7.15;N,7.64. Found: C,72.05;H,7.11;N,7.73.

Component B, mp 210.5–204.5° C. (corr) was identified by $^1$H NMR as the cis compound IVb (R=Ph) Anal. calc'd. for $C_{22}H_{26}N_2O_3$: 72.11;H,7.15;N,7.64. Found: C,71.77;H,7.14;N,7.54.

EXAMPLE 4

(±)trans-N-(8,9-dimethoxy-1,3,4,6,11,11a-hexahydro-2H-benzo [b]quinolizin-2-yl)-1,2,3,4-tetrahydro-2-naphthalenecarboxamide

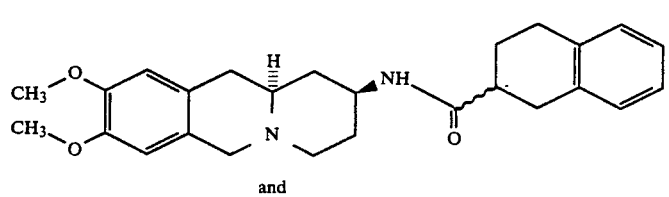

Component A (±)cis-N-(8,9-dimethoxy-1,3,4,6,11,11a-hexahydro-2H-benzo [b]quinolizin-2-yl)-1,2,3,4-tetrahydro-2-naphthalenecarboxamide

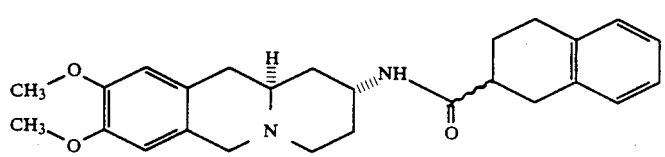

Component B

Following the procedure outlined in example 3, 8,9-dimethoxy-1,3,4,6,11,11a-hexahydro-2H-benzo [b]-quinolizin-2-amine (1.49 g) was acylated by 1,2,3,4-tetrahydronapthoyl chloride (derived from treatment of 1.00 g of acid with thionyl chloride) Flash chromatography (70:28 2 cyclohexane:isopropanol:NH$_4$OH) provided two diastereomeric compounds, a higher R$_f$ product (A, 0.97 g), and a lower R$_f$ product (B, 0.61 g). Recrystallization of each component from ethyl acetate/hexane afforded pure products.

Component A, mp 224–230° C (corr) was identified by $^1$H NMR as the trans compound IVa (R=tetrahydronaphthyl). Anal. calc'd. for $C_{26}H_{32}N_2O_3$: C,74.26;H,7.67; N,6.66. Found: C,74.14;H,7.72;N,6.60.

Component B, mp 155.5–159.5° C (corr) was identified by $^1$NMR as the cis compound IVb (R=tetrahydronaphthyl). Anal. calc'd. for $C_{26}H_{32}N_2O_3$: C,74.26;H,7.67; N,6.66. Found: C,73.76;H,7.75;N,6.63.

EXAMPLE 5 trans-N-(8,9-dimethoxy-1,3,4,6,11,11a-hexahydro-2H-benzo [b]quinolizin-2-yl)-2-benzofurancarboxamide

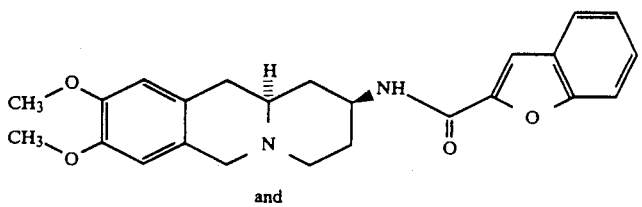

and cis-N-(8,9-dimethoxy-1,3,4,6,11,11a-hexahydro-2H-benzo (8 [b]quinolizin-2-yl)-2-benzofurnancarboxamide

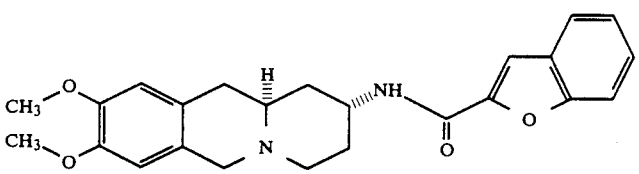

Following the procedure outlined in example 3, 8,9-dimethoxy-1,3,4,6,11,11a-hexahydro-2H-benzo [b]-quinolizin-2-amine (1.62 g) was acylated by benzofuran 2-carbonyl chloride (from 1.00 g of carboxylic acid with thionyl chloride). Flash chromatography (70:28:2 cyclohexane:isopropanol:NH$_4$OH) provided two diastereomeric compounds, a higher R$_f$ Product (A, 1.12 g), and a lower R$_f$ Product (B, 0.71 g). Recrystallization of each component from ethyl acetate/hexane afforded pure products.

Component A, mp 207–208° C (corr) was identified by $^1$H NMR as the trans compound IVa (R=2-benzofuranyl). Anal. calc'd. for $C_{24}H_{36}N_2O_4$: C,70.92;H,6.45; N,6.89. Found: C,70.78;H,6.54;N,6.63.

Component B, mp 240–243° C (corr) was identified by $^1$H NMR as the cis compound IVb (R=2-benzofuranyl). Anal. calc'd. for $C_{24}H_{36}N_2O_4$: C,70.92;H,6.45; N,6.89. Found: C,70.65;H,6.53;N,6.85.

EXAMPLE 6 trans-N-(8,9-dimethoxy-1,3,4,6,11,11a-hexahydro-2H-benzo [b]quinolizin-2-yl)acetamide Component A and cis-N-8,9-dimethoxy-1,3,4,6,11,11a-hexahydro-2-H-benzo [b]-quinolizin-2-yl)acetamide Component B Following the procedure outlined in example 3, 8,9-dimethoxy-1,3,4,6,11,11a-hexahydro-2H-benzo [b]-quinolizin-2-amine (0.787 g) was acylated by acetyl chloride. Column chromatogrpahy (70:28:2 chloroform: ethanol:NH$_4$OH) provided two diastereomeric compounds, a higher R$_f$ product (A, 0.35 g), and a lower R$_f$ product (B, 0.17 g). Recrystallization of each component from ethyl acetate/hexane afforded pure products.

Component A, mp 201–203° C (corr) was identified by $^1$H NMR as the trans compound IVa (R=CH$_3$). Anal. calc'd. for $C_{17}H_{24}N_2O_3$: C,67.08;H,7.95;N,9.20. Found: C,66.11;H,7.92;N,9.05.

Component B, mp 186.5–189.5° C (corr) was identified by $^1$H NMR as the cis compound IVb (R=CH$_3$).

Anal. calc'd. for $C_{17}H_{24}N_2O_3$: C,67.08;H,7.95;N,9.20. Found: C,66.27;H,7.97;N,9.07.

While the invention has been described and illustrated with reference to certain preparative embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of cardiac arrhythmia, dosage-related adverse effects, if any, and analogous considerations. Likewise, the specific pharmacological responses observed may vary according to and depending upon the particular active compounds selected or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow, and that such claims be interpreted as broadly a is reasonable.

What is claimed is:

1. A compound of the formula

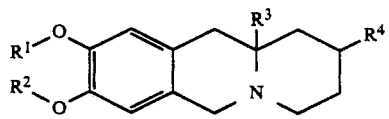

the pharmaceutically acceptable salts thereof, and the hydrated forms thereof, wherein $R^1$ and $R^2$ are independently alkyl of from 1 to 10 carbon atoms; $R^3$ is hydrogen in either a cis or a trans orientation; and $R^4$ is NHCOR' in either a cis or a trans orientation, wherein R' is alkyl of from 1 to 10 carbon atoms, cycloalkyl of from 3 to 8 carbon atoms, phenyl, phenyl substituted by alkyl of one to ten carbon atoms or alkoxy of from one to ten carbon atoms, halogen, or amino, fused phenylcycloalkyl, fused phenylcycloalkyl wherein phenyl is substituted by alkyl of from one to ten carbon atoms, benzofuranyl or benzofuranyl substituted by alkyl of from one to ten carbon atoms.

2. A compound of the general formula

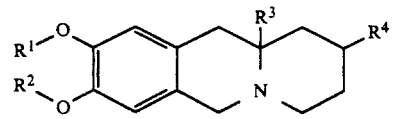

and or the pharmaceutically acceptable salts thereof, wherein $R^1$ and $R^2$ are independently alkyl of from 1 to 10 carbon atoms; $R^3$ is hydrogen in either the cis or trans orientation; and $R^4$ is NCHOR' in either the cis or trans orientation, wherein R' is alkyl of from 1 to 10 carbon atoms, cyclohexyl, phenyl, phenyl substituted by alkoxy of from one to ten carbon atoms, halogen or amino, fused phenylcyclohexyl, or benzofuranyl.

3. The compound as claimed in claim 2, in which $R^1$ and $R^2$ are both methyl.

4. The compound as claimed in claim 2, in which $R^3$ is hydrogen in the cis orientation.

5. The compound as claimed in claim 2, in which $R^4$ is in the cis orientation.

6. The compound as claimed in claim 2, in which $R^4$ is in the trans orientation.

7. A compound as claimed in claim 2, of the formula

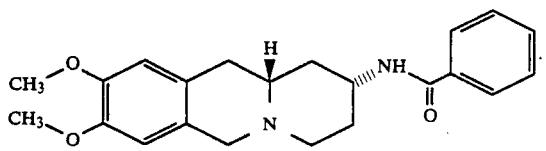

8. A compound as claimed in claim 2, of the formula

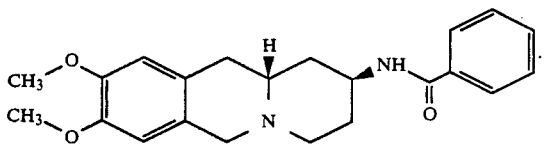

9. A compound as claimed in claim 2, of the formula

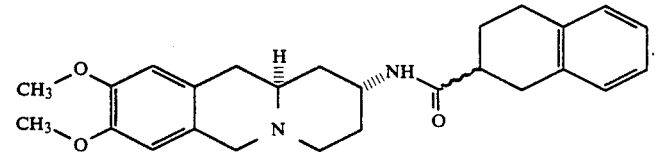

10. A compound as claimed in claim 2, of the formula

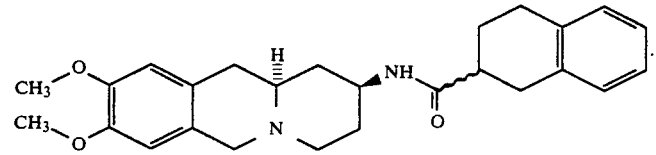

11. A compound as claimed in claim 2, of the formula

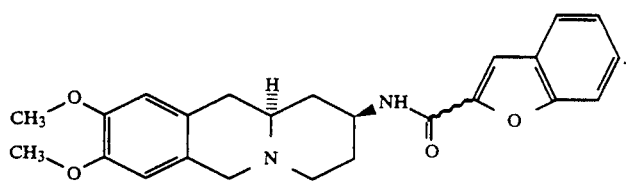

12. A compound as claimed in claim 2, of the formula

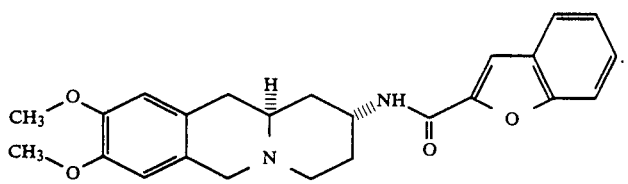

13. A compound as claimed in claim 2, of the formula

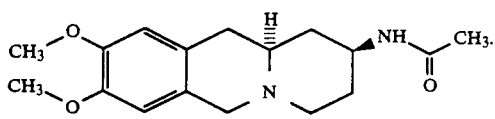

14. A compound as claimed in claim 2, of the formula

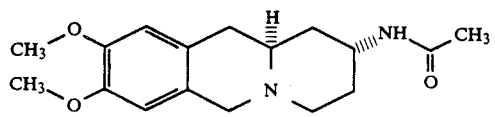

15. A pharmaceutical composition comprised of pharmaceutically acceptable carrier in combination with an amount of the compound as claimed in claim 1 effective to treat or prevent arrhythmia in a mammal.

16. The pharmaceutical composition as claimed in claim 15, wherein said compound is trans-N-(8,9-dimethoxy1, 3,4,6,11,11a-hexahydro-2H-benzo[b]quinolizin-2-yl) benzamide.

17. The pharmaceutical composition as claimed in claim 15, wherein said compound is cis-N-(8,9-dimethoxy-1, 3,4,6,11,11a-hexahydro-2H-benzo[b]quinolizin-2-yl) benzamide.

18. The pharmaceutical composition as claimed in claim 15, wherein said compound is (±)cis-N-(8,9-dimethoxy-1, 3,4,6,11,11a-hexahydro-2H-benzo[b] quinolizin-2-yl)-1,2,3,4-tetrahydro-2-naphthalenecarboxamide.

19. The pharmaceutical composition as claimed in claim 15, wherein said compound is trans-N-(8,9-dimethoxy-1, 3,4,6,11,11a-hexahydro-2H-benzo[b] quinolizin-2-Yl)-2-benzofurancarboxamide.

20. The pharmaceutical composition as claimed in claim 15, wherein said compound is cis-N-(8,9-dimethoxy-1, 3,4,6,11,11a-hexahydro-2H-benzo[b] quinolizin-2-yl)-2-benzofurancarboxamide.

21. The pharmaceutical composition as claimed in claim 15, wherein said compound is trans-N-(8,9-dimethoxy1, 3,4,6,11,11a-hexahydro-2H-benzo[b]quinolizin-2-yl) acetamide.

22. The pharmaceutical composition as claimed in claim 15, wherein said compound is cis-N-(8,9-dimethoxy- 1, 3,4,6,11,11a-hexahydro-2H-benzo[b]quinolizin-2-yl) acetamide.

23. A method of regulating cardiac arrythmias in a mammal, comprising administering to said mammal a pharmacologically effective amount of a compound as claimed in claim 1.

24. The method as claimed in claim 23, wherein said compound is trans-N-(8,9-dimethoxy-1,3,4,6,11,11a-hexahydro-2H-benzo [b]quinolizin-2-yl)benzamide.

25. The method as claimed in claim 23, wherein said compound is cis-N-(8,9-dimethoxy-1,3,4,6,11,11a-hexahydro-2H-benzo [b]quinolizin-2-yl)benzamide.

26. The method as claimed in claim 23, wherein said compound is (±)cis-N-(8,9-dimethoxy-1,3,4,6,11,11a-hexahydro-2H-benzo [b]quinolizin-2-yl)-1,2,3,4-tetrahydro-2-naphthalenecarboxamide.

27. The method as claimed in claim 23, wherein said compound is trans-N-(8,9-dimethoxy-1,3,4,6,11,11a-hexahydro-2H-benzo [b]quinolizin-2-yl)-2-benzofurancarboxamide.

28. The method as claimed in claim 23, wherein said compound is cis-N-(8,9-dimethoxy-1,3,4,6,11,11a-hexahydro-2H-benzo [b]quinolizin-2-yl)-2-benzofurancarboxamide.

29. The method as claimed in claim 23, wherein said compound is trans-N-(8,9-dimethoxy-1,3,4,6,11,11a-hexahydro-2H-benzo [b]quinolizin-2-yl)acetamide.

30. The method as claimed in claim 23, wherein said compound is cis-N-(8,9-dimethoxy-1,3,4,6,11,11a-hexahydro-2H-benzo [b]quinolizin-2-yl)acetamide.

31. A method of prolonging repolarization of cardiac cells during a cardiac action potential in a mammal, comprising administering to such mammal a pharmacologically effective amount of a compound as claimed in claim 1.

* * * * *

UNITED STATES PATENT AND TRADEMARK OFFICE
CERTIFICATE OF CORRECTION

PATENT NO. : 4,992,446
DATED : Feb. 12, 1991
INVENTOR(S) : Fowler

It is certified that error appears in the above-identified patent and that said Letters Patent is hereby corrected as shown below:

Column 3, line 2, structure reading

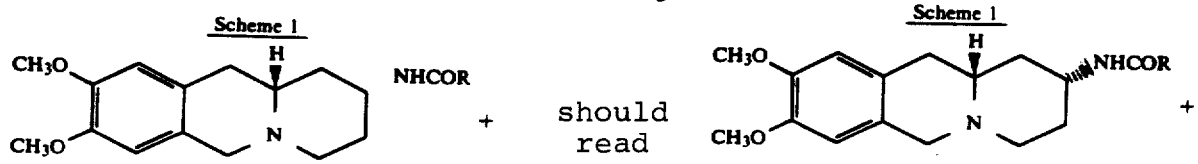

Column 5, line 26, reading "Svnthesis" should read -- Synthesis --

Column 5, line 27, reading "1.3,4,5,11,11a-hexahydro-9-dimethoxy-2H-benzo[b]-quinolizin-2-amine" should read -- 1,3,4,5,11,11a-hexahydro-8,9-dimethyl-2H-benzo[b]-quinolizin-2-amine --.

Column 5, line 30, reading "2H-benzo [b]quinolizin-2-one" should read -- 2H-benzo[b]-quinolizin-2-one --.

Column 5, line 42 reading "afforded 2 71 g" should read -- afforded 2.71g --.

Column 5, line 49, reading "(CDCL$_3$) 6 6.56" should read --(CDCL$_3$) δ 6.56 --.

Column 6, line 24, reading "A Solution of 8,g-dimethoxy" should read -- A solution of 8,9-dimethoxy --.

Column 7, line 14, reading "(70:28 2)" should read --(70:28:2) --.

Column 7, line 43, reading "benzo (8 [b]quinolizin-2-yl)" should read -- benzo [b]quinolizin-2-yl) --.

UNITED STATES PATENT AND TRADEMARK OFFICE
CERTIFICATE OF CORRECTION

PATENT NO. : 4,992,446

DATED : Feb. 12, 1991

INVENTOR(S) : Fowler

It is certified that error appears in the above-identified patent and that said Letters Patent is hereby corrected as shown below:

Column 8, line 57, reading "Column chromatogrpahy" should read -- Column chromatography --.

Column 9, line 56, reading "2. A compound of the general formula" should read -- 2. A compound of the formula --.

Column 10, line 6, reading "and or the pharmaoeutically" should read -- and or the pharmaceutically --.

Column 11, line 61, reading "zin-2-Yl)-2-benzofurancarboxamide." should read -- zin-2-yl)-2-benzofurancarboxamide.--.

Signed and Sealed this

Eighth Day of December, 1992

*Attest:*

DOUGLAS B. COMER

*Attesting Officer*  *Acting Commissioner of Patents and Trademarks*